US009011376B2

(12) United States Patent
Genosar et al.

(10) Patent No.: US 9,011,376 B2
(45) Date of Patent: Apr. 21, 2015

(54) DRUG DELIVERY DEVICE WITH ELECTRICALLY CONTROLLED VOLUME CHANGING MEANS

(75) Inventors: Amir Genosar, Lafayette, CO (US); Jonathan Goldstein, Jerusalem (IL)

(73) Assignee: SteadyMed Ltd., Tel Aviv (IL)

( * ) Notice: Subject to any disclaimer, the term of this patent is extended or adjusted under 35 U.S.C. 154(b) by 705 days.

(21) Appl. No.: 11/996,468

(22) PCT Filed: Jul. 3, 2006

(86) PCT No.: PCT/IL2006/000769
§ 371 (c)(1),
(2), (4) Date: Nov. 19, 2008

(87) PCT Pub. No.: WO2007/010522
PCT Pub. Date: Jan. 25, 2007

(65) Prior Publication Data
US 2009/0093772 A1 Apr. 9, 2009

(30) Foreign Application Priority Data
Jul. 21, 2005 (IL) .......................................... 169807

(51) Int. Cl.
*A61M 1/00* (2006.01)
*A61M 37/00* (2006.01)
(Continued)

(52) U.S. Cl.
CPC .............. *A61M 5/14244* (2013.01); *A61B 5/01* (2013.01); *A61B 5/14532* (2013.01);
(Continued)

(58) Field of Classification Search
CPC ............ A61B 5/14532; A61B 5/4839; A61M 2005/14252; A61M 2005/14513; A61M 5/14244; A61M 5/14526; A61M 5/14566; A61M 5/1723
USPC .............. 604/890.1, 288.01–288.04, 20, 150, 604/197, 114, 264, 246, 19, 21, 27, 65, 152, 604/131, 151, 891.1
See application file for complete search history.

(56) References Cited

U.S. PATENT DOCUMENTS 4,842,598 A * 6/1989 Tran ........................... 604/891.1
5,062,834 A 11/1991 Gross et al.
(Continued)

FOREIGN PATENT DOCUMENTS

DE 3621846 A1 1/1988
DE 198 09 483 9/1999
(Continued)

OTHER PUBLICATIONS

Jae Hyunn Lee, Hyand Mok Lee, Soonho Ahn, Battery dimensional changes occurring during charge/discharge cycles thin rect angualr lithium ion and polymer cells, 2003, Journal of Power Sources, 119-121, pp. 833-837.*
(Continued)

*Primary Examiner* — Bhisma Mehta
*Assistant Examiner* — Bradley G Thomas, Jr.
(74) *Attorney, Agent, or Firm* — Kilpatrick Townsend & Stockton LLP (57) ABSTRACT

The present invention provides a drug delivery device comprising a drug reservoir chamber (15) containing a substance (16) to be delivered in fluid connection with a drug administration means (17) and (18), and a hydraulic control chamber (9) containing an electrically controlled, non-gassing, volume changing means (13), a coupling means (14) coupling said hydraulic control chamber (9) to said drug chamber (15), the arrangement being such that a change in the electrical control means (11) causes a change in the volume of the volume changing means (13), the volume change being conveyed by the coupling means (14) to the drug chamber (15) such that the substance (16) is expelled from the drug chamber (15) towards the drug administration means (17) and (18).

36 Claims, 9 Drawing Sheets (51) Int. Cl.
  *A61M 5/00* (2006.01)
  *A61K 9/22* (2006.01)
  *A61M 5/142* (2006.01)
  *A61M 5/145* (2006.01)
  *A61B 5/01* (2006.01)
  *A61B 5/145* (2006.01)
  *A61B 5/00* (2006.01)
  *A61M 5/172* (2006.01)

(52) U.S. Cl.
  CPC ......... *A61B 5/4839* (2013.01); *A61M 5/14526* (2013.01); *A61M 5/1454* (2013.01); *A61M 5/14566* (2013.01); *A61M 5/14593* (2013.01); *A61M 5/1723* (2013.01); *A61M 2005/14252* (2013.01); *A61M 2005/14513* (2013.01); *A61M 2230/201* (2013.01)

(56) References Cited

U.S. PATENT DOCUMENTS

| | | | |
|---|---|---|---|
| 5,108,852 A * | 4/1992 | Tomantschger et al. | 429/66 |
| 5,109,850 A | 5/1992 | Blanco et al. | |
| 5,318,557 A | 6/1994 | Gross | |
| 5,354,264 A | 10/1994 | Bae et al. | |
| 5,436,372 A | 7/1995 | Yoshida et al. | |
| 5,438,249 A | 8/1995 | Chang et al. | |
| 5,505,706 A | 4/1996 | Maus et al. | |
| 5,527,288 A | 6/1996 | Gross et al. | |
| 5,643,207 A | 7/1997 | Rise | |
| 5,677,083 A | 10/1997 | Tomiyama | |
| 5,814,020 A | 9/1998 | Gross | |
| 5,848,991 A | 12/1998 | Gross et al. | |
| 6,186,982 B1 | 2/2001 | Gross et al. | |
| 6,322,532 B1 * | 11/2001 | D'Sa et al. | 604/22 |
| 6,377,848 B1 * | 4/2002 | Garde et al. | 604/20 |
| 6,400,489 B1 | 6/2002 | Suzuki et al. | |
| 6,506,520 B1 | 1/2003 | Inoue et al. | |
| 6,534,218 B1 | 3/2003 | Okada et al. | |
| 6,537,250 B1 | 3/2003 | Kriesel | |
| 6,577,039 B2 | 6/2003 | Ishida et al. | |
| 6,589,229 B1 * | 7/2003 | Connelly et al. | 604/890.1 |
| 6,733,485 B1 | 5/2004 | Whitehurst et al. | |
| 6,982,514 B1 | 1/2006 | Lu et al. | |
| 7,242,134 B2 | 7/2007 | Wallace et al. | |
| 7,541,715 B2 | 6/2009 | Chiang et al. | |
| 2002/0169439 A1 * | 11/2002 | Flaherty | 604/891.1 |
| 2003/0014014 A1 | 1/2003 | Nitzan | |
| 2004/0059282 A1 * | 3/2004 | Flock et al. | 604/20 |
| 2004/0068224 A1 | 4/2004 | Couvillon et al. | |
| 2004/0115068 A1 | 6/2004 | Hansen et al. | |
| 2005/0096587 A1 * | 5/2005 | Santini et al. | 604/66 |
| 2006/0069344 A1 * | 3/2006 | Southam et al. | 604/20 |

FOREIGN PATENT DOCUMENTS

| | | |
|---|---|---|
| EP | 0 676 214 | 10/1995 |
| JP | 02-131376 | 5/1990 |
| JP | 04-127885 | 4/1992 |
| WO | WO 97/10012 | 3/1997 |
| WO | WO 01/21234 A1 | 3/2001 |
| WO | WO 2004/067066 | 2/2003 |
| WO | WO 2005/124918 A2 | 12/2005 |

OTHER PUBLICATIONS

European Patent Office, "Opposition Division Decision of European Patent No. EP-B-2 015 806," dated May 5, 2012, 15 pages.

Fairbairn, A., "Statement of Grounds of Appeal pertaining to European Patent No. 2 015 806," Sep. 12, 2012, 13 pages.

Notice of Opposition to a European Patent of EP Patent No. 2 015 806 B1, dated Jun. 1, 2010, 16 pages total.

* cited by examiner

DRUG DELIVERY DEVICE WITH ELECTRICALLY CONTROLLED VOLUME CHANGING MEANS

FIELD OF THE INVENTION

The present invention relates to the field of drug delivery and is directed to a drug-delivery device driven by an electrically-controlled volume change. More particularly, this invention relates to an electrically-controlled non-gassing volume-changing means such as an electrochemical cell or an electroactive polymer, which drives a drug-delivery mechanism, wherein the delivery rate can be very precisely controlled by an electrical circuit.

BACKGROUND OF THE INVENTION

There are numerous kinds of electrochemical cells, the common element being that applying an electrical charge to such a cell causes a chemical change or change in the ionic structure of such a cell. Many types of electrochemical cells comprise electrodes and electrolyte, in which the chemical reaction between said chemicals is driven by discharging or charging said electrodes. Such a cell can be either a passive cell or a battery cell. In a passive cell, electricity needs to be introduced into the cell in order to "drive" the chemical reaction. In a battery cell or fuel cell, the cell itself generates electricity as the reaction runs, providing that a discharge circuit is provided. In the case of a passive cell (or a battery on charge), the rate of reaction is determined by the electrical power applied; whereas in a battery cell which is discharging, the control over the energy consumption determines the rate of discharge of the battery. The definition of battery cells herein includes not only conventional type batteries (using either "wet" or "dry" chemistry) but also (a) lithium "shuttle" type batteries in which the process is that ions in the electrolyte shuttle back and forth between the electrodes as opposed to participating in a conventional chemical reaction; and (b) sealed fuel cells in which a fixed starting amount of fuel is used up as the cell discharges. The present invention applies to all the above types of cell, providing only that the chemical process involved is such that it causes a volume change within the cell as the process proceeds.

In the field of battery cells, the volume change generated as the battery charges or discharges is a known yet undesirable side effect, said effect being mentioned in the prior art. For example, US Patent Application 20040115530 describes a method of preventing the detrimental effects of the volume change of the active material in a lead-acid battery cell. However, in the present invention, such "undesirable" volume changes are exploited in order to deliver a useful feature: precise, controlled drug-delivery such as that required for slow-infusion or implanted medical devices.

Numerous types of inexpensive drug-delivery mechanisms are known in the art, typically employing a gas-driven infusion principle. U.S. Pat. Nos. 5,318,557 and 5,527,288 describe an inexpensive, gas-driven infusion device which can be manufactured sufficiently inexpensively in order to constitute a disposable product. The embodiments described therein employ an electrolytic cell for gas production as per U.S. Pat. No. 5,062,834. A similar gas-driven device is described in U.S. Pat. No. 5,354,264. This device utilizes gas pressure from free oxygen and hydrogen derived from the electrolysis of water at the electrodes in negatively charged polymeric hydrogels. Said device ensures that the gas generated remains within the walls of the gas chamber by making said walls "rigid and impermeable to gases". In all these devices, the gas pressure forces the infusion of the drugs through appropriate means into the body, with the pressure being dependent on the rate of electrolysis, which is in turn controlled by an electric current. A further class of devices uses the same gas-driven principle, but generates this gas by chemical rather than electrical means. For example, U.S. Pat. No. 5,814,020, hereby incorporated by reference, describes a gas-powered infusion device where the gas is generated either by an electrolytic cell or by the reaction between citric acid and sodium bicarbonate; said reaction generating carbon dioxide and water.

The central problem with these gas-driven devices is that they all employ a gas-filled chamber in order to drive the drug infusion. As gases are very susceptible to changes in ambient temperature and air pressure, the danger of employing this principle is that a significant and undesirable change in the flow-rate will occur as such temperature or pressure changes occur. For example, a loss of pressure in an airplane could result in a sudden bolus being delivered at an inappropriate time. Similarly, a drop in temperature could result in the drug infusion stopping. For these reasons, despite massive development efforts, these products have faced considerable commercial obstacles to implementation. The prior art confirms the problematic nature of this issue: In a partial attempt to address this issue, U.S. Pat. No. 6,186,982 describes a flow-regulation chamber appropriate to the above-described devices which attempts to compensate for such temperature and/or pressure changes. Nonetheless, this issue of heat and pressure sensitivity is an inherent disadvantage inhibiting the commercialization of these products. Additionally, even when the surrounding conditions are constant, these technologies suffer from the disadvantage of providing a time-lagged response to the control system. For example, if the system's control requires a complete halt of the drug delivery, the residual gas pressure will keep pushing the drug out.

Further prior art in this field includes (a) MEMS-based pumps in which a miniature pump is implemented on a silicon chip using integrated-circuit fabrication techniques, such as the Chronojet™ from Debiotech S. A. (Lausanne, Switzerland); (b) those in which a piezo-electric pumping mechanism is used such as U.S. Pat. No. 6,589,229; and (c) those which use SME wire technology such as the OmniPod™ product from Insulet, Inc. (Bedford, Mass., USA). All these approaches entail complicated mass-manufacturing issues, which have either not yet been solved or require elaborate control mechanisms and fine tolerances; both of which greatly increase costs to the point where it is difficult to produce a disposable product.

Another major concern with existing drug delivery devices is the difficulty of making such a complex mechanism (and its associated electronics) waterproof. This issue is tackled either by the users being very careful not to get it wet, or by a complex sealing of the the mechanism package. Said sealing is inherently difficult with permanent pump devices where new disposable infusion sets need to be periodically attached to the device.

Accordingly, there is a need for an inexpensive drug-delivery device which is capable of very precise actions while only requiring low manufacturing tolerances, and is simple to operate with minimal requirements for internal control/feedback mechanisms.

It is also the object of the present invention to provide a drug-delivery device which is relatively insensitive to temperature and pressure changes.

It is a further object of the invention to provide a drug-delivery device where an electrochemical cell provides the main power source for said delivery.

It is a still further object of this invention to provide a drug-delivery device with a minimum of moving parts.

It is a still further object of this invention to provide a drug-delivery device with inherent position determination.

It is a still further object of this invention to provide a drug-delivery device which does not suffer from a lag in response time.

It is a still further object of this invention to provide a drug-delivery device which is inherently waterproof.

It is still further object of the present invention to provide a drug-delivery device where control and maintenance issues are simpler than in existing approaches and with less potential failure modes.

These and other objects of this invention will become more evident in the summary of the invention and in the description of the preferred embodiment.

SUMMARY OF THE INVENTION

According to the present invention there is now provided a delivery device for drugs or other substances (henceforth a "drug-delivery device") comprising a drug reservoir chamber containing a substance to be delivered in fluid connection with a drug administration means, and a hydraulic control chamber containing an electrically controlled, non-gassing, volume changing means, a coupling means coupling said hydraulic control chamber to said drug chamber, the arrangement being such that a change in said electrical control means causes a change in the volume of the volume changing means, said volume change being conveyed by said coupling means to said drug chamber such that said substance is expelled from said drug chamber towards said drug administration means.

In preferred embodiments of the present invention said drug administration means is selected from the group consisting of cannulas, cannula arrays, exit ports and transdermal patches.

Preferably said electrical control means includes an electric circuit connected to said volume changing means via electrical contacts.

In further preferred embodiments of the present invention said volume-changing means is an electrochemical cell comprising electrodes and electrolyte, and said electrical contacts are connected to said electrodes.

In especially preferred embodiments of the present invention said volume-changing means is an electroactive polymer wherein said electrical contacts are attached to points on the surface of said polymer.

Preferably said electrochemical cell is a passive cell wherein the combined volume of said electrodes and electrolyte changes in response to an electrical current applied to said electrical contacts.

Especially preferred is an embodiment wherein said electrochemical cell is a battery cell wherein the combined volume of said electrodes and electrolyte changes its volume as its electrical charge is depleted on application of a load across said electrical contacts.

In said preferred embodiments preferably said battery cell is selected from the group consisting of a lead-acid battery, a dry cell battery, a nickel-cadmium battery, a lithium ion battery and a fuel cell.

Further preferred is an embodiment wherein said battery cell further comprises an internal gas volume which is consumed by a chemical reaction within said battery cell taking place on discharge of said battery cell.

Preferably said battery is a zinc-air battery.

Especially preferred are embodiments wherein said battery cell serves to power at least some of the electrical and electronic elements of said device.

Preferably said drug-delivery device is disposable.

Alternatively, said drug-delivery device is partly disposable.

In some preferred embodiments said drug-delivery device is an implantable device.

In further preferred embodiments said drug-delivery device further comprises a filling means.

Preferably said drug-delivery device further comprises a battery recharging means.

Especially preferred are drug delivery devices wherein said drug-delivery device is a multiple-use device.

In preferred embodiments of the present invention said drug-delivery device is a patch-type pump, and preferably said patch-type pump is attached to the body by a means comprising an adhesion means, a strap, a clasp and combinations thereof.

In other preferred embodiments of the present invention said drug-delivery device further comprises an auto-insertion means, and preferably said auto-insertion means serves to insert the administration means.

Alternatively, said auto-insertion means automatically activates the drug-infusion device.

In further preferred embodiments of the present invention said drug-delivery mechanism further comprises a plurality of drug chambers, and preferably said drug-delivery device includes means for the mixing of the drugs from said plurality of drug chambers.

In other preferred embodiments of the present invention said drug-delivery device further comprises a plurality of control cells.

In preferred embodiments of the present invention said drug chamber includes means enabling the intake of body fluids; said fluids serving to dilute a drug for subsequent administration by said drug-delivery device on reversion to its normal operating mode.

Preferably said device further comprises means for sampling body fluids for analysis.

In yet further preferred embodiments of the present invention said drug-delivery device further comprises communications means to remote devices selected from the group consisting of magnetic induction, infra-red, and RF devices.

Preferably said administration means further comprises a safety feature to protect against accidental contact or injury.

In preferred embodiments of the present invention the change of volume of the drug chamber is proportional to the change in the volume of the control chamber.

Preferably the change in the volume of the volume changing means is proportional to an external non-gassing electric perturbation.

Preferably said control cell is a hydraulic control cell.

In especially preferred embodiments of the present invention there is provided a drug-delivery device comprising a drug chamber containing a substance to be delivered and an hydraulic control chamber, said drug chamber and control chamber being coupled by means such that the change of volume of the drug chamber is proportional to the change in the volume of the volume changing means within the control chamber, and wherein said change of volume of the drug chamber causes the drug to be dispensed via said administration means, and wherein the change of the volume of the volume changing means within the control chamber is proportional to an external non-gassing electric perturbation.

Preferably the present invention provides a drug delivery device comprising a drug reservoir chamber containing a substance to be delivered in fluid connection with a drug administration means, and a hydraulic control chamber containing an electrically controlled, non-gassing, volume changing means, a coupling means coupling said hydraulic control chamber to said drug chamber, the arrangement being such that a change in said electrical control means causes a change in the volume of the volume changing means, said volume change being conveyed by said coupling means to said drug chamber such that said substance is expelled from said drug chamber towards said drug administration means.

In especially preferred embodiment of the present invention said drug reservoir chamber is coupled to said hydraulic control chamber via a displaceable wall; such that the volume change of the volume-changing means serves to control the rate of delivery of the drug.

Preferably said drug reservoir chamber is coupled to said hydraulic control chamber via a piston arrangement; such that the volume change of the volume-changing means serves to control the rate of delivery of the drug.

Said drug-delivery device may be employed in a number of different configurations, including but not limited to: implantable devices, slow-infusion devices, disposable infusion devices, partially disposable infusion devices and patch-pumps. Given the absence of motors and other such sensitive components, the drug-delivery device of the present invention is inherently simple to render waterproof. The volume-changing means used in said device is such that the charging or discharging of this means causes a volume change within it. This volume change is then conveyed hydraulically via a displaceable wall or piston arrangement to the drug chamber, causing the drug therein to be delivered via the administration means. The volume-changing means together with its hydraulic fluid and displaceable wall constitute the control cell of the device of the present invention. In the case that the volume-changing means is an electrochemical cell, said hydraulic fluid is typically the electrolyte of said cell. In the case that the volume-changing means is a solid-state one such as an electroactive polymer or a lithium-ion battery, then the hydraulic fluid is a fluid in contact with said means. Thus, in either case, the control cell is defined such that all enclosed volumes are considered as part of the same cell and thus the displaceable wall of the present invention is any part of said control cell which is displaceable by said volume change. For example, said displaceable wall may be a part of the housing surrounding the electrodes of an electrochemical cell, or it may equally well be a piston remote from such electrodes but in fluid connection to the electrolyte. In a further example, the control cell may comprise an electroactive polymer which expands on charging surrounded by a hydraulic fluid such an oil. In a preferred embodiment, the control cell is a battery cell in which a volume change occurs when the battery cell discharges.

The displaceable wall of the present invention can take a number of forms, including but not limited to: a rigid yet displaceable section of the wall, a flexible wall section, a liquid-liquid interface and a piston. A simple example of a cell with a displaceable wall is a cylindrical cell with a rigid circular cap sealed against one end by means of an elastomeric gasket, said cap being capable of moving up or down as the charge/discharge proceeds. In all such cases, the displaceable section of the wall moves in response to the volume change generated. In the drug delivery-device of the present invention, said movement serves to expel a drug from a drug chamber in mechanical connection with said displaceable wall.

In a preferred embodiment, the control cell employed within the present invention pushes a piston of a drug chamber such that the drug contained within said drug chamber is forced through an administration means into the body of a patient. Said administration means can include a conventional cannula as known in the art, or any other means whereby the drug is introduced into the body. Such means can include arrays of short cannulas such as the SimpleChoice™ patch product (SpectRx, Inc., Norcross, Ga., USA), arrays of micro-needles, non-invasive transdermal devices, or auto needle insertion means. Alternatively, where the drug-delivery device of the present invention is an implantable one, the delivery means can be any exit port or tube leading from the device to the required location in the body of the patient.

Where the control cell of the drug-delivery device of the present invention utilizes an electrochemical volume-changing means, a number of electrochemical reaction systems are appropriate. They include but are not limited to:

1. The lead-acid reaction: $Pb+PbO_2+2H_2SO_4=2PbSO_4+2H_2O$ whereby one gm mole of reactants 642 gm (154 cc) contracts on discharge by 13%. In this system the positive electrode is lead dioxide, the negative electrode is lead and the electrolyte is sulfuric acid. Discharge to the reaction products (in this case lead sulfate and sulfuric acid further diluted with water) which have different densities and molecular weights from the starting materials, causes the net volume contraction.
2. The nickel-cadmium cell reaction: $Cd+2NiOOH+2H_2O=Cd(OH)_2+2Ni(OH)_2$ in which one gm mole of reactants 332 gm (90 cc) contracts on discharge by 15%.
3. The dry cell reaction: $Zn+2MnO_2=ZnO+Mn_2O_3$ whereby one gm mole of reactants 239 gm (44 cc) expands on discharge by 13%.
4. The formate/$MnO_2$ fuel cell: $HCOOK+2MnO_2+KOH=K_2CO_3+2MnOOH$ whereby one gm mole of reactants 314 gm (106 cc) contracts on discharge by 8%. In this case the negative electrode is an aqueous solution of potassium formate "fuel" in contact with a catalytic electrode, the positive electrode is manganese dioxide and the electrolyte is aqueous potassium hydroxide. The fuel gaseous oxidation product, carbon dioxide, reacts in-situ with the alkaline electrolyte, forming liquid phase potassium carbonate.

Alternatively, the volume-changing means may be a solid-state one such as a lithium-ion type battery or an electroactive polymer such as those described in IEEE Spectrum Online ("Electric Flex"), June 2004.

In either case, where the volume-changing process is a reversible one, then such a control cell can also allow refilling of the drug-delivery device of the present invention, which can be an important feature for implantable devices.

This approach to drug-delivery device design has a number of advantages. As there is no pump or motor in the conventional sense, there are very few parts, and essentially only the piston or other displaceable wall is a moving part. By using a minimum number of moving parts, failure modes and maintenance issues are minimized. Additionally, noise factors such as friction, backlash and assembly tolerance issues are minimized. Accordingly, very precise control of the drug-delivery device is enabled by this design. In fact, providing that the non-displaceable walls of the control cell remain rigid, the resolution of the achievable movement is limited only by the accuracy of the power supply and discharge circuitry; something which can be provided to a very high degree using electronic circuitry known in the art. This is especially important in the case of implantable drug-delivery devices, where drug delivery rates in the picoliter range are required so as to be able to deliver drug quantities in the milliliter range over a period of months or years. Additionally, advantageously this approach provides the ability to determine the volume of drug delivered, purely by knowing the electric charge/discharge performed. Despite this, it should be apparent to one skilled in the art that, where required, it is possible to further provide (a) a feedback or control circuit which incorporates position-detection elements such that the information concerning the volume of drug delivered is not solely dependent on monitoring the charge/discharge performed; and (b) pressure sensors and other feedback and safety means can be incorporated into said control circuitry and logic.

The invention will now be described in connection with certain preferred embodiments, with reference to the following illustrative figures so that it may be more fully understood.

With specific reference now to the figures in detail, it is stressed that the particulars shown are by way of example and for purposes of illustrative discussion of the preferred embodiments of the present invention only and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

BRIEF DESCRIPTION OF THE DRAWINGS

The invention is herein described, by way of example only, with reference to the accompanying drawings, wherein.

DETAILED DESCRIPTION OF THE DRAWINGS

The present invention will be described in detail according to the preferred embodiments illustrated in the accompanying drawings. Like reference numerals are used to identify identical components in the various views.

Figure 1:
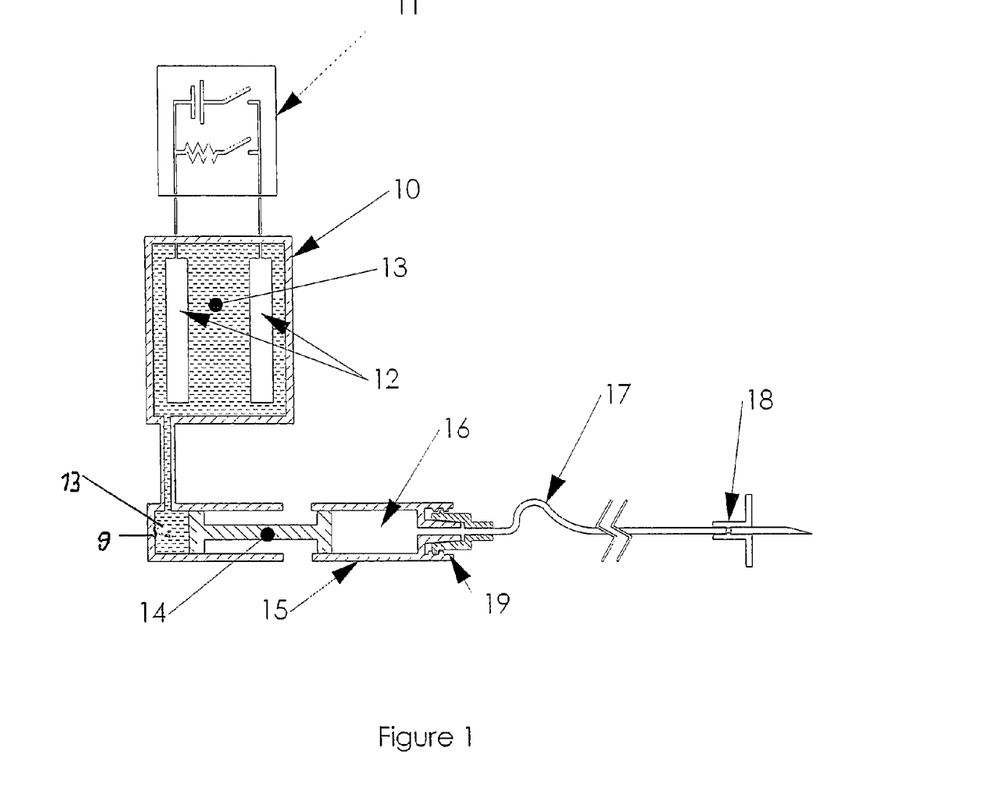
FIG. 1 provides a block diagram of the overall drug-delivery device, showing its main components.

Referring to FIG. 1, a simplified block diagram of the drug-delivery device of the present invention is shown in its simplest configuration where an electrochemical control cell constitutes the volume-changing means. In this embodiment an electrochemical cell 10 which undergoes a volume increase on charging is charged via an electrical or electronic control circuit 11. Said circuit 11 can serve to either provide a charge to, or enable a discharge from, the cell 10; and for this reason both a battery and a resistor are shown within the block diagram of said circuit 11 for a schematic representation of its functionality. In the example shown, the battery within the circuit 11 in connected via contacts to the electrodes 12 and serves to charge the cell 10, such that the combined volume of the electrodes 12 and electrolytes 13 increases. The device includes hydraulic control chamber 9 which is in fluid connected with cell 10 and which therefore also contains the non-gassing volume changing means which are electrolytes 13. As the only displaceable wall in the cell 10 and its connected hydraulic control chamber 9 is the piston 14, said piston 14 is forced into the drug chamber 15, causing the drug 16 contained therein to be expelled along the conduit 17 to a cannula 18 or other administration means. Said administration means can be an integrated continuation of the drug chamber or a separated assembly introduced to the drug cell port through a custom connector or a standard connector such as Lauer Lock connector 19. As will be clear to one skilled in the art, the administration means can be any means whereby the drug or other substance delivered by the device enters the patient's body, including but not limited to an exit port in an implantable version of the device, and a cannula or cannula array or a transdermal patch for an external device.

Figure 2A:
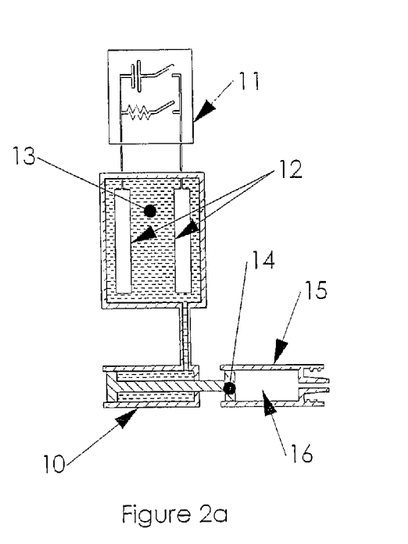
FIG. 2 provides a block diagram of a preferred embodiment of the drug-delivery device showing different coupling arrangements between the drug chamber and the control cell.

Referring now to FIG. 2a, a preferred embodiment of the drug-delivery device of the present invention is shown. In this preferred embodiment, the electrochemical or control cell 10 is a battery cell and the primary function of the electric circuit 11 is to perform a controlled discharge of said cell. Advantageously, this embodiment obviates the requirement for a separate battery to drive the drug-delivery device, as the cell producing the volume change is itself the battery. This provides a saving in the parts count, which in turn reduces the cost and weight of the device. Although there are battery cells (such as dry cells) which experience an increase of volume as they are discharged, in this preferred embodiment, the volume within the cell 10 decreases as it is discharged. Thus in this preferred embodiment the electronic control unit 11 serves to discharge the cell 10 such that the combined volume of the electrodes 12 and electrolyte 13 contracts. As this contraction occurs, the piston 14 advances into the drug cell 15, causing the drug 16 to be expelled. In this embodiment, the cell 10 is filled with either liquid or gel 13, where the electrode plates 12 serve to complete the battery system and this liquid or gel 13 serves to pull the piston 14 forward into the drug cell 15. The connection between the two cylinders shown in FIG. 2a is a serial one, but the connection can equally well be a parallel one as shown in FIG. 2b.

Figure 2B:
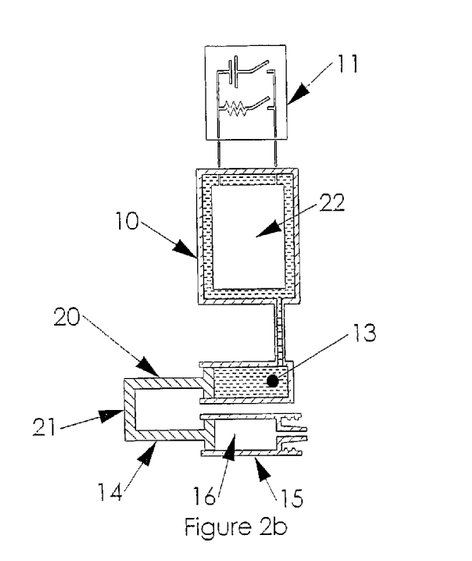
Figure 2C:
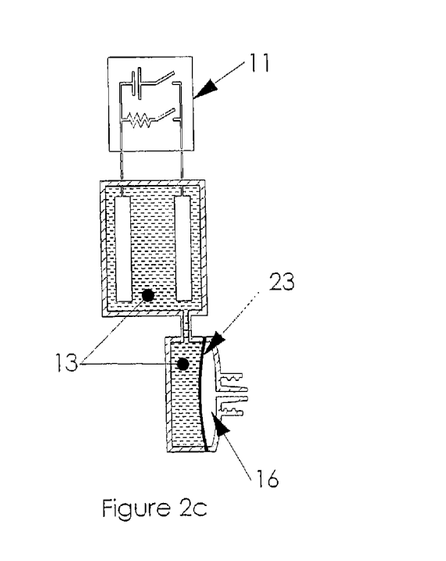
Figure 2D:
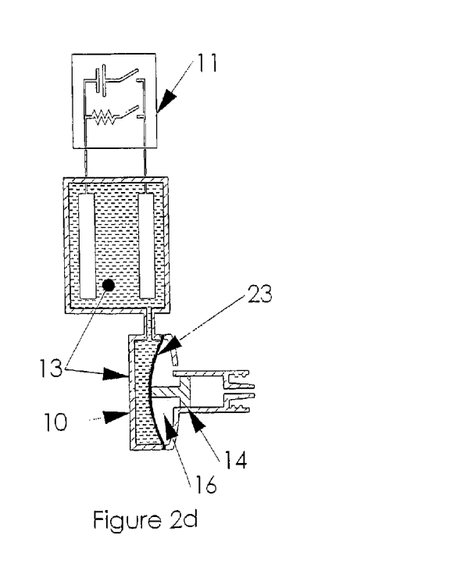

Referring now to FIG. 2b, a mechanical link 21 serves to couple the piston 14 of the drug chamber 15 with the piston 20 of a control cell 10. Said control cell 10 comprises a sealed volume-changing element 22 and a hydraulic fluid 13 external to said sealed unit. Said sealed volume-changing element 22 can be: (a) an electrochemical cell as described above; (b) a solid-state device such as an electroactive polymer, with two contacts attaching it to the electric circuit 11, or (c) a solid-state battery such as a lithium-ion battery. In this preferred embodiment, the volume contraction of the sealed unit 22 is conveyed to the rest of the mechanism by said hydraulic fluid 13 as opposed to being conveyed by the electrolyte participating in the chemical reaction within an electrochemical cell. Advantageously, when employing an electrochemical cell within the sealed unit 22, this arrangement isolates the electrolyte from the piston arrangement, simplifying the materials choice while also ensuring better isolation of chemicals in case of leakage. It will be clear to one skilled in the art that the coupling between the control cell 10 and the drug chamber 15 may be achieved via any coupling means including but not limited to mechanical bar mechanisms, mechanical trains, pulleys, etc., resulting in either proportional motion or a more complex exponential correlation. For example, FIG. 2c shows a non piston-based mechanical arrangement, where flexible wall 23 constitutes the displaceable wall between the control cell 10 and the drug chamber 15. Said flexible wall 23 may either exert pressure on the drug 16 directly or via the use of a piston 14 as shown in FIG. 2d.

In a preferred embodiment, this system implements one of the battery or fuel cell systems such as those described above, including but not limited to nickel-cadmium (NiCad), Formate/MnO2 fuel cell and dry cells. However, purely to demonstrate the volume change concept, the volume change associated with the well-known lead acid battery system is provided in the table below which provides the molecular weights, densities and volumes of the reactants (on the left-hand side) and the products of this reaction on the right-hand side:

|  | Pb | $PbO_2$ | $2H_2SO_4$ | $2PbSO_4$ | $2H_2O$ |
| --- | --- | --- | --- | --- | --- |
| Mol wt (gm) | 207 | 239 | 196 | 606 | 36 |
| Density | 11.3 | 9.4 | 1.8 | 6.2 | 1 |
| Volumes (cc) | 18.3 | 25.4 | 108.8 | 97.7 | 36 |
| Total volume |  | 153.5 |  | 133.7 |  |

As will be seen from this table, the total volume of the reactants and products, given one mole of reagents, is reduced on discharge from 153.5 cc to 133.7 cc, which is a 19.8/153.5 contraction, or a 13% decrease. The above reaction operates at 2V and according to Faradays Law provides 2 Faradays (53.6 Ahr). A volume change of 0.2 cc for example, would thus require a cell of capacity 0.2/19.8×53.6 Ah=0.54 Ah.

Note that the present invention includes the use of any kind of non-gassing volume-changing means where said means is connected via contacts to an electrical or electronic circuit; such that the passing of current across said contacts causes a volume change. At its simplest, this circuit is just a resistor via which a battery-type volume-changing means is discharged. Alternatively, the circuit is a battery and the volume-changing means is a passive electrochemical cell or electroactive polymer. Where an electrochemical cell is employed as the volume-changing means, the volume change is typically the change of the combined volume of liquids, solids, pastes, and gels within the cell. In the case of a fuel cell, the internal fuel is consumed and thus the volume decreases. Note that a fuel cell will further comprise additional elements including a fuel compartment and an inert catalytic electrode to provide the fuel oxidation reaction. In its simplest embodiment a fuel anode coupled with an oxide cathode such as manganese dioxide could be used; although air could be used as the cathode instead. A further special case is the use of batteries which react with air such as zinc-air batteries. In this case, in the present invention the air is stored internally to the battery casing, such that as this air is consumed, the battery volume contracts.

Figure 3A:
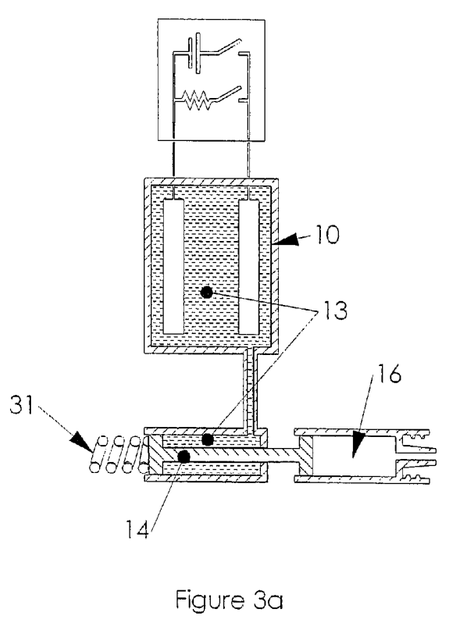
FIG. 3 provides a block diagram of a further preferred embodiment of said device, further comprising a spring.
Figure 3B:
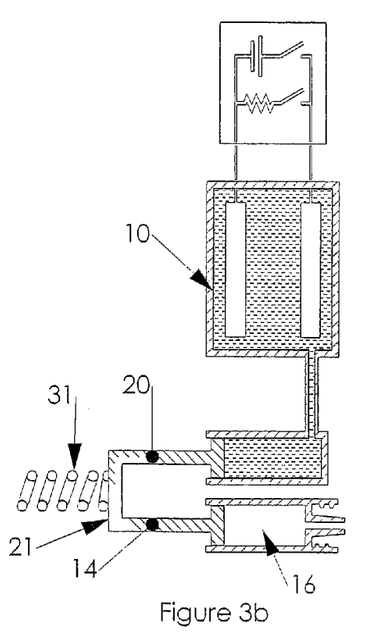

Referring now to FIG. 3, a further preferred embodiment of the drug-delivery device of the present invention is shown. In this preferred embodiment, a reverse-brake configuration is employed, whereby the motion of the piston 14 due to the driving force of the spring 31 is restrained by the electrolytic fluid 13. FIG. 3a shows said reverse-brake configuration where the two cylinders (cell and drug) are positioned in series such that the movement of the piston 14 is driven by the spring 31; and FIG. 3b shows the configuration where said cylinders are positioned in parallel such that the mechanical link 21 couples the movement of the pistons (20 and 14) into them. The advantages of this approach and further details of its implementation are described in co-pending published application WO2004067066 by one of the same authors; hereby incorporated by reference. It will be obvious to one skilled in the art that the connection between the cylinders (i.e. the drug chamber and the electrochemical cell) can be any kind of mechanical hydraulic, magnetic or other coupling means known in the art; and that said coupling action may result in either a proportional or an exponential correlation between a multiplicity of such drug chambers 16 and a multiplicity of such cells 10. Note that in certain systems according to this embodiment the driving force will be the combination of the force exerted by the spring and the contraction/expansion of the cell.

Whereas the embodiments above describe relatively simple configurations of the drug-delivery device of the present invention, the general principles involved in said invention enable the implementation of a large number of further embodiments; said further embodiments addressing further issues in such devices, such as refilling, drug dilution and implantable versions. For example, referring now to FIG. 4, an additional electrochemical cell 41 is employed in order to enable two-way motion of the piston 14 without an external power source; said motion proceeding as follows: (a) As a first cell 10 is depleted, the piston 14 is driven into the drug chamber 15 as per the previous embodiments. (b) As the volume within the second cell 41 contracts, the piston assembly 43 is withdrawn into its housing 42; said assembly 43 also constituting the housing of the cylinder surrounding piston 14. As the housing 42 is connected by rigid member 44 to the drug cylinder 15, the withdrawal of the piston assembly 43 into said housing 42 causes the piston 14 to be (slowly) extracted from the drug chamber 15. Thus, purely by controlling the discharging of two electrochemical cells (10 and 41), motion of the piston 14 into and out of the drug chamber is achieved. This two-way motion is especially advantageous where refilling of the drug chamber is required.

Figure 4:
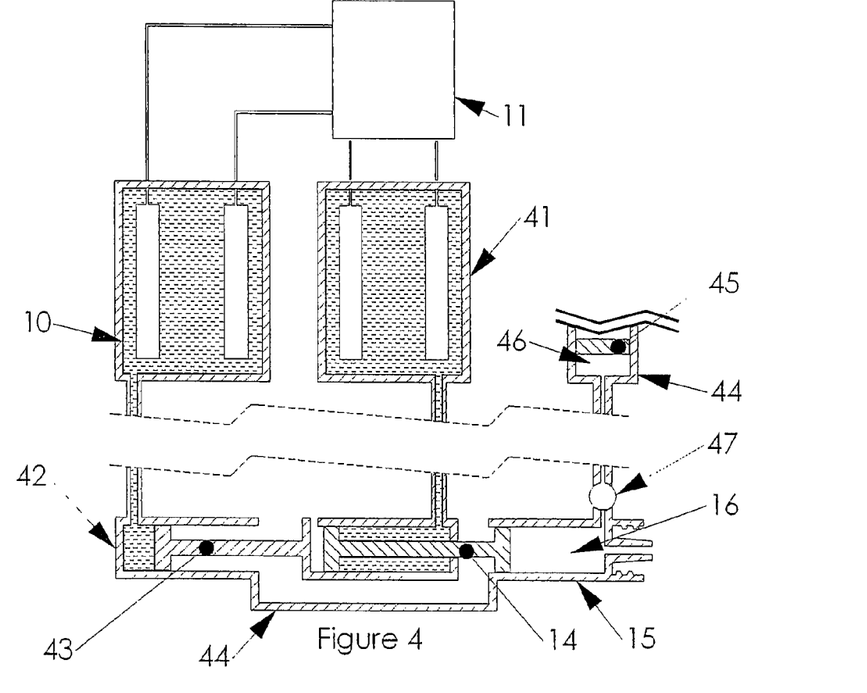
FIG. 4 provides a block diagram showing the use of two control cells and the delivery of two-way motion.

A major objective when designing an implantable drug-delivery device is to enable it to work over an extended period that could extend to several years. One solution to this issue is to provide a filling port accessible from the patient's skin. However, such filling ports are notoriously susceptible to contamination, making this approach a very problematic route. The invention of the present invention enables an improved approach whereby a second drug chamber 44 contains a highly concentrated form of the drug to be delivered. After each completed cycle of drug delivery (i.e. when the piston 14 has advanced to the right-hand end of the drug chamber 15), the two-way motion of the mechanism is exploited to gradually withdraw this piston 14 to the left. As said piston 14 is withdrawn, a small amount of the drug concentrate 46 from the second or reservoir chamber 44 is introduced to the drug chamber 15 via non-return valve 47 due to the pressure of displaceable wall 45 on said drug concentrate 46. Further, as the piston 14 continues to withdraw, body fluids will enter the drug chamber 15 through said chamber's outlet port; said fluids serving to dissolve and/or otherwise dilute said drug concentrate 46. On reversing the direction of the piston 14 yet again when the drug chamber has refilled, the now diluted drug will start to be delivered as before; i.e. the next cycle can begin. As will be obvious to one skilled in the art, the concentrated drug can be in either liquid or solid form, and the mechanism as described above can provide drug delivery over an extended period without requiring external refilling. Likewise, the ability to use the drug-delivery device of the present invention to perform intake of body fluids enables said device to further incorporate various body fluid sampling and/or analysis elements.

Figure 5:
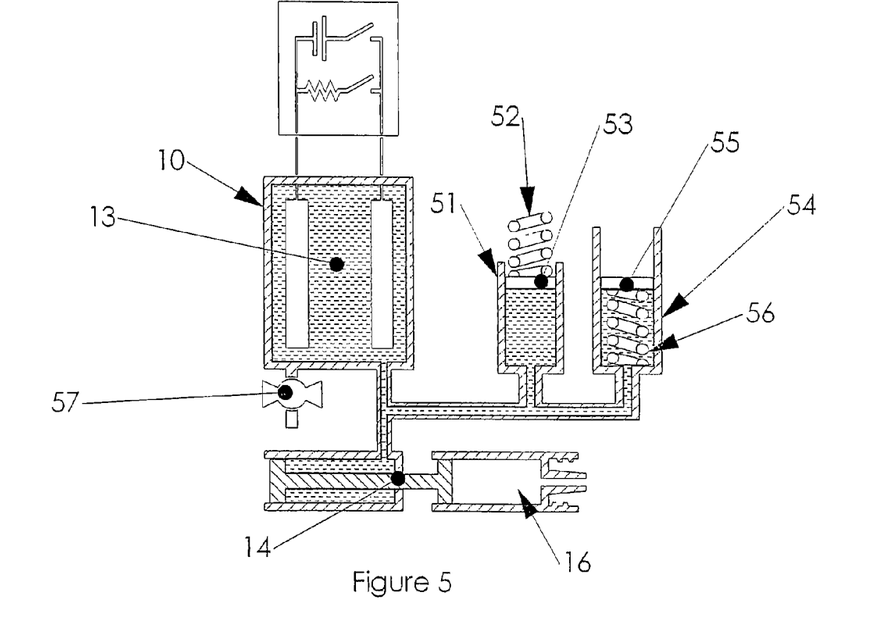
FIGS. 5 and 6 provide block diagrams showing the addition of further hydraulic elements.

All the above embodiments relate to the case where the volume enclosing the entire hydraulic system remains constant except for the displaceable wall or piston. Accordingly, in this case, the volume-changing means is the only changing factor and thus its change is directly expressed in the movement of the piston. Referring now to FIG. 5, the addition of further hydraulic elements to the system is presented, whereby the volume enclosing this hydraulic system can be increased or decreased. These hydraulic elements include: (1) an injector 51 whereby, on release of the spring 52, the inner volume of said injector 51 is subtracted from the total volume of this hydraulic system, thereby causing the piston 14 to advance and expel the drug 16; (2) an extractor 54 where, on release of its internal spring 56, said extractor causes the piston 14 to retract, thereby adding to the total volume of this hydraulic system; and (3) a filling and/or drainage port that can be used in conjunction with the reversal of either of the above steps. As will be obvious to those skilled in the art displacement caused by such springs could equally well be performed by numberous alternative actuation means, including but not limited to electric motors such as linear motors, solenoids, magnetic couping or a further electro-chemical actuator.

Figure 6A:
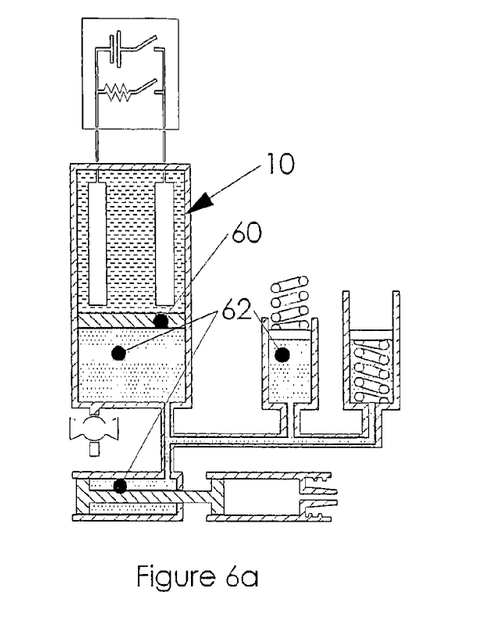

As will be obvious to one skilled in the art, it is not necessary to use the electrolyte as the hydraulic fluid throughout the entire system. Instead, and referring now to FIG. 6a, a displaceable wall in the form of a moveable partition 60 is located within the electrochemical cell 10 such that the volume change produced by said cell is conveyed via a hydraulic fluid 62 to the rest of the system. This arrangement is advantageous as per the description of FIG. 2b above. The figure shows a 1:1 volume displacement ratio but obviously the movable partition and cylinder can have different diameters on each end, resulting in a different fluid displacement ratio.

Figure 6B:
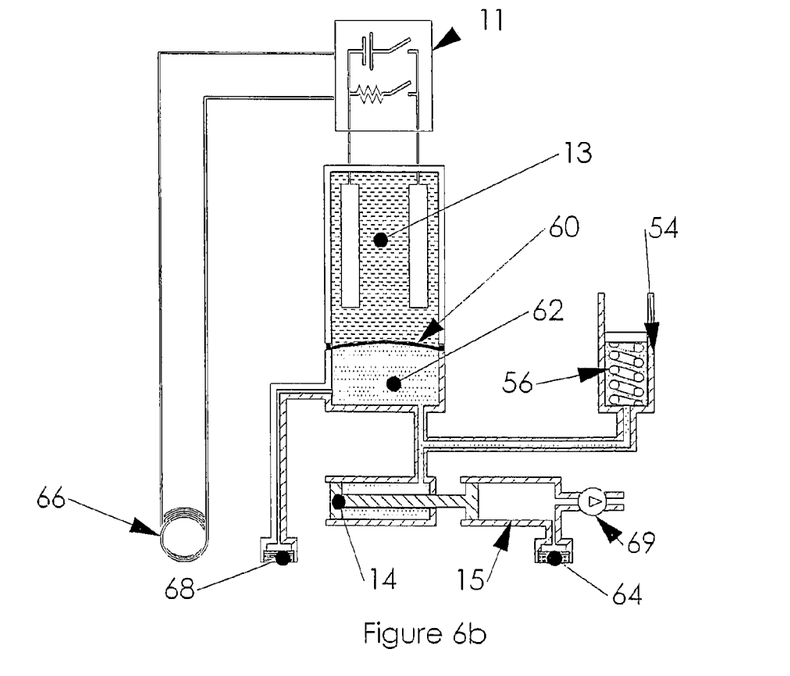

Referring now to FIG. 6b, a preferred embodiment of the drug-delivery device of the present invention is shown, optimized for implantable use, with an external filling port. This embodiment illustrates a number of potential ways in which the piston 14 can be withdrawn so that the drug chamber 15 can be refilled via filling port 64, typically by means of a septum. One way in which the piston 14 can be withdrawn is by charging the electrochemical cell 10, either by direct external electrical connection (not shown) or, preferably, by a magnetic induction coil 66. A second way to accomplish this objective is to use an injector 54 as per FIG. 5 above; and the third is the introduction of hydraulic fluid 62 via a hydraulic fluid filling port 68, also equipped with a septum. This embodiment also illustrates the use of a flexible membrane as the displaceable wall 60 within the electrochemical cell 10, and the use of a non-return valve 69 at the outlet of the drug chamber 15, to prevent ingress of body fluids.

Referring now to FIG. 7, a preferred embodiment of a miniature implementation of the drug-delivery device of the present invention is shown. FIG. 7a shows an exploded isometric view of said device, comprising a printed circuit board (PCB) 70, a rigid lower cover 72 of the control cell which also serves as part of the outer housing of the device, the flexible upper wall 74 of the drug chamber, hydraulic jacks 75 which are in fluid connection with the control cell below and attached to a rigid plate 77 above, and a septum 76. Referring now to FIG. 7b, the view from below of the PCB is provided, showing two electrodes 12 on its surface. The electric or electronic control circuit 11 may be implemented in the same PCB, terminating at the electrodes 12. In its simplest embodiment, the circuit 11 is simply a resistor that is placed across the ends of the electrodes 12 when an external rim to the device (not shown) is rotated to the "on" position. Referring now to FIG. 7c, a cross-sectional view of the device is shown where the functional role of all the above components is shown. Starting with the control cell 10, it is seen that this cell is formed between the rigid lower cover 72 of the device and the PCB 70 above, and contains electrodes 12 and an electrolyte 13 which serves as a hydraulic fluid. The liquid volume of said cell 10 is shown to extend through holes in the PCB 70 to the hydraulic jacks. As the liquid volume in said cell 10 is reduced, the jacks 75 retract toward the PCB 70, thereby exerting force on the rigid plate 77 to which they are attached. Note that the drug chamber 15 is formed between the PCB 70 and the flexible upper wall 74. As the rigid plate 70 is pulled towards the PCB 70 by the contraction of the hydraulic jacks 75, the drug 16 enclosed within the drug chamber 15 is gradually expelled through the cannula 17. In this embodiment, the cannula 17 is typically a Teflon™ one, which is inserted into the body using a needle 79 which is inserted via the septum 76. As known in the art, additional elements incorporated in the insertion means may include a safety feature to protect against accidental contact or injury.

Figure 7A:
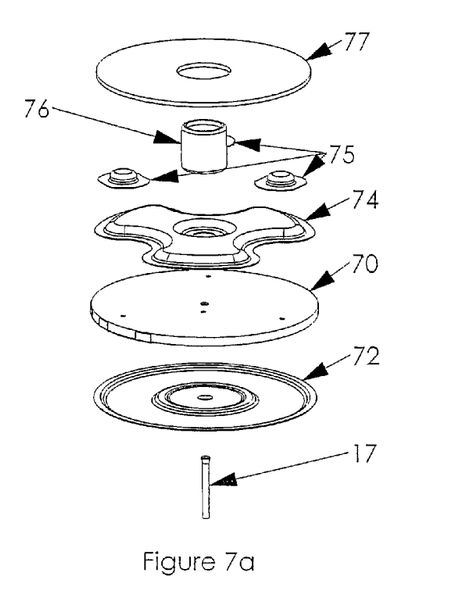
FIG. 7 provides isometric and cross-sectional figures showing a preferred miniature embodiment of the device.
Figure 7B:
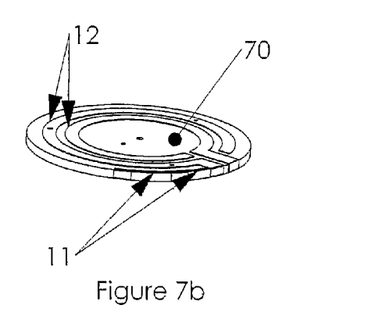
Figure 7C:
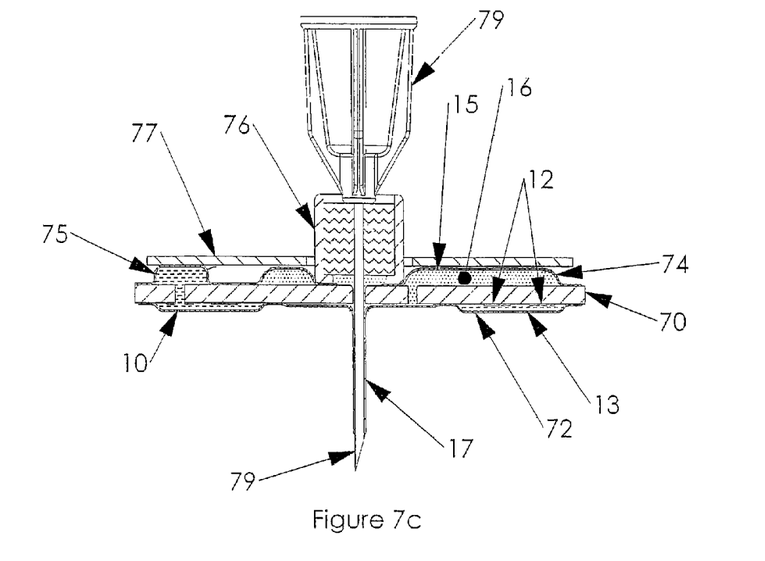
Figure 7D:
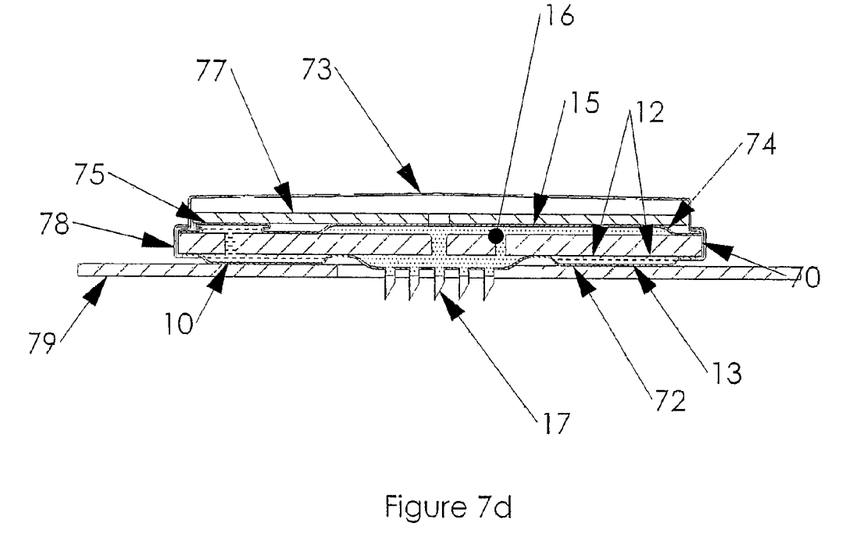

Referring now to FIG. 7d, a further preferred embodiment of the drug-delivery device of the present invention is shown. In this embodiment, the needle 79 and septum 76 are obviated as the drug administration means in this case is a mini-cannula or micro-cannula array 17 which does not require external insertion means. This figure shows the mechanism at an advanced dispensing stage so that the hydraulic jacks 75 and the flexible wall 74 serving as the upper wall of the drug chamber 15 are partly empty or collapsed. It also shows the entire assembly further comprising an adhesive patch 79 for attaching the device to the body and a stainless steel enclosure 78 surrounding at the least top and sides of the device, where said enclosure 78 can also serve as a rotating component used as a switch to activate the device and/or regulate the dosing rate. Said rotating action can also provide a lock/lock release to the dispensing mechanism to avoid inadvertent activation. Note that in both this embodiment and the previous one, a hole is required in the rigid plate 77 so that air trapped between it and the flexible wall 74 is evacuated as the plate 77 descends. The device of the present invention may be further provided with an air compensation means implemented in its external enclosure so that the mechanism may freely contract as it operates. Said means may include a flexible wall, a gas-permeable (and preferably hydrophobic) membrane, or simply an air hole.

Note that both of the above embodiments (as per FIGS. 7c and 7d) can be provided with either a single-use or a multi-use insertion device; whereby the drug-delivery device will be attached to the skin and have the cannula(s) inserted into the body by a single and simple non-disturbing action. In a further preferred arrangement, said insertion action also automatically operates the device. Additionally, the materials used for the cannulas or mini/micro-cannulas and/or the adhesive patch may include an eluting element to gradually release an anesthetic or anti-inflammatory drug to the skin. The use of eluting materials for fabricating stents is well known in the art, and this approach can be used for example on the rigid cannulas to minimize the pain involved. Alternative means of attaching the drug-delivery device of the present invention include straps and clasps.

Figures 8A, 8B, 8C, 8D, 8E:
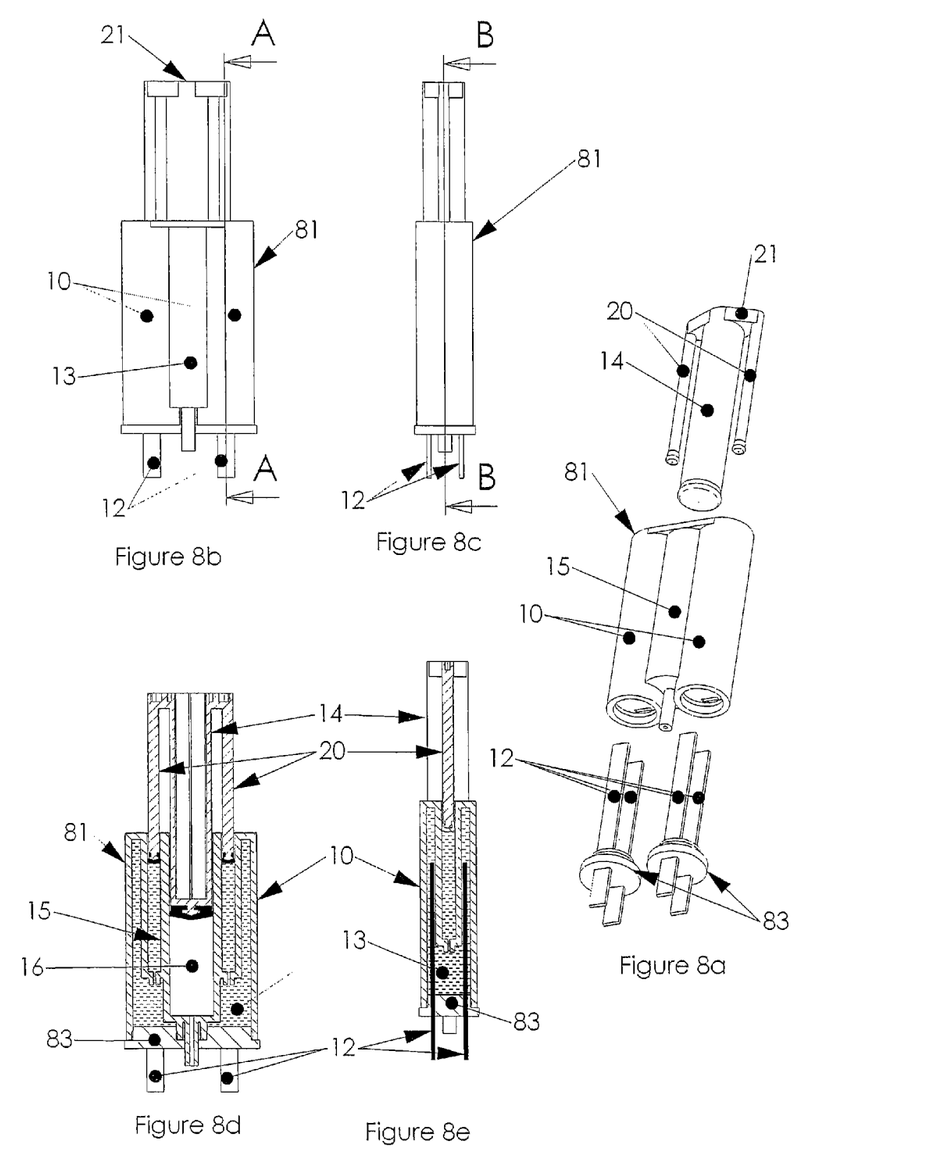
FIG. 8 provides isometric and cross-sectional figures showing a preferred embodiment of the device employing dual control cells.

Referring now to FIG. 8, various views of a preferred embodiment of the drug-delivery device of the present invention based on the "parallel" design of FIG. 3b above are provided. Referring now to FIG. 8a, an isometric exploded view of the device of the present invention is provided, showing a piston assembly comprising control cell pistons 20 and a drug cell piston 14, joined by a mechanical link 21; and a housing 81 containing the cylinders for said pistons, said housing 81 providing the cylinders for the drug chamber piston 14 and the control cell piston 20. Note that in this embodiment two control cells 10 are provided in parallel for safety reasons, such that even if one of them should develop a leak, the brake effect discussed in relation to FIG. 3 above would continue to operate and a massive drug dose to the patient would be prevented. The electrode assemblies 83 each hold two electrode plates 12, with a fixed spacing. Referring now to FIGS. 8b and 8c; two planar views (from above and from the side respectively) of this embodiment are shown; the lines A-A and B-B provide the cut line for showing the cross sections shown in FIGS. 8d and 8e respectively. Referring now to FIG. 8d, a cross-sectional view of the assembled device is provided showing how the pistons enter their respective cylinders. In a preferred embodiment the area ratio of the two types of pistons enables the determination of the ratio effect required. For example, using a 10:1 ratio between the area of the drug chamber piston 14 and that of the cell piston would enable a relatively small change in the volume of the drug chamber (say 0.2 cc) to drive a drug-infusion of ten times that amount (2 cc). Obviously, reversing the ratio can enable the opposite effect. Also clearly seen in this cross-sectional view is the way in which the electrochemical control cell 10 contains one contiguous volume, part of which is inside a cylinder and part (the majority) is external to said cylinder. The excess of electrolyte and electrodes size enables longer strokes as the shrinkage of the cell is limited. Referring now to FIG. 8e, the placing of the electrodes within this latter, external volume, is see. This structure enables the electrodes 12 to contact the electrolyte as a whole, while only a subsection of the electrolyte is gradually depleted from the narrow cylinder. In combination with the piston ration described above, this arrangement enables a relatively small discharge to power a significant drug infusion. In this preferred embodiment, the pistons are free to move in accordance with the expansion/contraction of the volume in the cell 10. Various kinds of O-rings or other means known in the art may be used to seal the interface between the pistons and their respective cylinders such that the system is maintained sealed.

Regarding the electrical or electronic control circuit of the drug-delivery device of the present invention, it will be apparent to those skilled in the art that a wide range of electronic control systems (not shown) may be incorporated within (or interfaced to) said device. Said range includes: (a) microprocessor-controlled variable-resistance or load elements for controlled discharge of the cell; (b) removable control units that enable a semi-disposable device to be constructed whereby all or part of the control circuitry may be moved from disposable section to disposable section; (c) systems comprising a remote-control element; (d) systems that interface to a flow-control feedback element monitoring the actual drug delivery rate, either directly or indirectly; (e) an interface control unit that receives signals related to medical parameters such as blood-glucose levels, other blood-analyte levels and body temperature; and (f) any combination of the above. Advantageously, where the control cell is also a battery cell, said electronics circuit and/or electronic control systems may e at least partially powered by the very depletion of power that drives the drug-delivery device, thereby in many cases obviating the need to provide a battery to power the electronics of such a device. Additionally, in the case of an implanted device, the design may further employ embedded electronics sealed by resin casting or other sealing means known in the art, and various communication means including but not limited to magnetic coupling transmission, RF or IR transmission.

It is obvious to those skilled in the art that more sophisticated embodiments are possible which combines a multiplicity of drug cells and a multiplicity of electrochemical cells, in every possible arrangement or interaction with each other, and combining every possible coupling means including hydraulic, mechanic, magnetic, etc.

Preferred chemical systems for an electrochemical cell within the drug-delivery device of the present invention are those which are non-gassing or in which there is minimal parasitic gas production. Nevertheless, in the case that the selected chemical reaction does generate gas, said gas may either be vented via a gas-permeable membrane or recombined via a catalytic plug such as those made by Hoppecke Battery Company, Germany. As all cell walls other than the displaceable one must remain fixed and rigid in order to maintain the accuracy of the slow-infusion device, it is important that such membrane be provided with an appropriate support structure so as not to detract from the rigid structure of the cell. These gas eliminating means are arranged in a fashion that efficiently operates in every operational orientation of the device. Suitable gas-permeable membranes include Fluoropore™ membrane from Millipore Inc. (Billerica, Mass., USA) and Emflon™ from Pall Inc. (East Hills, N.Y., USA).

While the invention has been shown herein in what is presently conceived to be the most practical and preferred embodiment thereof, it will be apparent to those of ordinary skill in the art that many modifications may be made thereof within the scope of the invention, which scope is to be accorded the broadest interpretation of the appended claims so as to encompass all equivalent structures and devices.

The invention claimed is:

1. A drug delivery device comprising: a drug reservoir chamber containing a substance to be delivered, said drug reservoir chamber in fluid connection with a drug administration element, and a control chamber comprising a battery, said battery comprising a housing, electrodes and an electrolyte, said housing surrounding said electrodes and said electrolyte, said battery being configured such that the combined volume of said electrodes and electrolyte changes upon the discharge of said battery, and a mechanical coupling element coupling said battery to said drug reservoir chamber, the arrangement being such that a change in said combined volume during discharging of said battery displaces a portion of the housing, and said displacement of the housing is mechanically conveyed by said mechanical coupling element to said drug chamber resulting in expulsion of said substance from said drug reservoir chamber towards said drug administration element.

2. A drug delivery device according to claim 1, wherein said drug administration element is selected from the group consisting of cannulas, cannula arrays, exit ports and transdermal patches.

3. A drug delivery device according to claim 2, wherein said administration element further comprises a safety feature to protect against accidental contact or injury.

4. A drug delivery device according to claim 1, wherein the control chamber further comprises an electric circuit connected to said battery via electrical contacts configured to discharge electrical current therefrom.

5. A drug delivery device according to claim 4, wherein said electrical contacts are connected to said electrodes.

6. A drug delivery device according to claim 4, wherein said battery comprises at least one electrochemical cell comprising electrodes and electrolyte, and wherein said electrical contacts are connected to said electrodes.

7. A drug delivery device according to claim 6, wherein said at least one electrochemical cell is a passive cell wherein the combined volume of said electrodes and electrolyte changes in response to an electrical current removed from said electrical contacts.

8. A drug delivery device according to claim 6, wherein the combined volume of said electrodes and electrolyte changes its volume as its electrical charge is depleted on application of a load across said electrical contacts.

9. A drug delivery device according to claim 1, wherein said battery is selected from the group consisting of a lead-acid battery, a dry cell battery, a nickel-cadmium battery, a lithium ion battery and a fuel cell.

10. A drug delivery device according to claim 1, wherein said battery is a zinc-air battery.

11. A drug delivery device according to claim 1, wherein said drug-delivery device is disposable.

12. A drug delivery device according to claim 1, wherein said drug-delivery device is partly disposable.

13. A drug delivery device according to claim 1, wherein said drug-delivery device is an implantable device.

14. A drug delivery device according to claim 1, wherein said drug-delivery device further comprises a filling element.

15. A drug delivery device according to claim 1, wherein said drug-delivery device is a multiple-use device.

16. A drug delivery device according to claim 1, wherein said drug-delivery device is a patch-type pump.

17. A drug delivery device according to claim 16, wherein said patch-type pump is attached to the body by an attachment element comprising an adhesion element, a strap, a clasp and combinations thereof 18. A drug delivery device according to claim 1, wherein said drug-delivery device further comprises an auto-insertion element.

19. A drug delivery device according to claim 18, wherein said auto-insertion element serves to insert the drug administration element.

20. A drug delivery device according to claim 18, wherein said auto-insertion element automatically activates the drug-infusion device.

21. A drug delivery device according to claim 1, wherein said drug reservoir chamber further comprises a plurality of drug chambers.

22. A drug delivery device according to claim 21, wherein said drug-delivery device includes a mixing element for mixing of the drugs from said plurality of drug chambers.

23. A drug delivery device according to claim 1 wherein said drug-delivery device further comprises a plurality of control chambers.

24. A drug delivery device according to claim 1, wherein said drug chamber includes an intake element for intake of body fluids; said fluids serving to dilute a drug for subsequent administration by said drug-delivery device on reversion to its normal operating mode.

25. A drug delivery device according to claim 24, wherein said device further comprises a sampling element for sampling body fluids for analysis.

26. A drug delivery device according to claim 1, wherein said drug-delivery device further comprises a communication element for communicating with remote devices selected from the group consisting of magnetic induction, infra-red, and radiofrequency devices.

27. A drug delivery device according to claim 1, wherein the change of volume of the drug reservoir chamber is proportional to the change in the volume of the control chamber upon the discharge of the battery.

28. A drug delivery device according to claim 1, wherein the change in the volume of the electrodes and the electrolyte is proportional to an external electric perturbation upon the discharge of the battery.

29. A drug-delivery device according to claim 1, wherein the change of the volume within the battery is proportional to an external electric perturbation.

30. A drug delivery device according to claim 1, wherein said drug reservoir chamber is coupled to said control chamber via a displaceable wall; such that the volume change of the electrodes and the electrolyte serves to control the rate of delivery of the drug.

31. A drug delivery device according to claim 1, wherein said mechanical coupling element comprises a piston arrangement.

32. A drug delivery device comprising:
  a drug reservoir chamber containing a substance to be delivered, said drug reservoir chamber in fluid connection with a drug administration element, and
  a control chamber comprising a battery, said battery comprising a housing, a zinc anode, a cathode and an electrolyte, said housing surrounding said anode, said cathode, and said electrolyte, said battery being configured such that the combined volume of said zinc anode and cathode and electrolyte expands upon the discharge of said battery, and
  a mechanical coupling element coupling said battery to said drug reservoir chamber, the arrangement being such that a change in said combined volume during discharging of said battery displaces a portion of the housing, and said displacement of the housing is mechanically conveyed by said mechanical coupling element to said drug chamber resulting in expulsion of said substance from said drug chamber towards said drug administration element.

33. The drug delivery device of claim 32, wherein said battery comprises an $MnO_2$ cathode.

34. The drug delivery device according to claim 32, wherein said drug administration element is selected from the group consisting of cannulas, cannula arrays, exit ports and transdermal patches.

35. The drug delivery device according to claim 32, wherein said drug-delivery device is disposable.

36. The drug delivery device according to claim 32, wherein said mechanical coupling element is hydraulically coupled with the control chamber and the drug reservoir chamber.

* * * * *

UNITED STATES PATENT AND TRADEMARK OFFICE
CERTIFICATE OF CORRECTION

| | |
|---|---|
| PATENT NO. | : 9,011,376 B2 |
| APPLICATION NO. | : 11/996468 |
| DATED | : April 21, 2015 |
| INVENTOR(S) | : Amir Genosar and Jonathan Goldstein |

It is certified that error appears in the above-identified patent and that said Letters Patent is hereby corrected as shown below:

In the specification

Column 15, line 29, please replace "thereof" with -- thereof. --

Signed and Sealed this
Twenty-seventh Day of October, 2015

Michelle K. Lee
*Director of the United States Patent and Trademark Office*